United States Patent [19]

Carr

[11] Patent Number: 4,758,308
[45] Date of Patent: Jul. 19, 1988

[54] SYSTEM FOR MONITORING CONTAMINANTS WITH A DETECTOR IN A PAPER PULP STREAM

[76] Inventor: Wayne F. Carr, 2229 Palisades Dr., Appleton, Wis. 54915

[21] Appl. No.: 708,429

[22] Filed: Mar. 5, 1985

[51] Int. Cl.$^4$ .................. D21F 7/06; G01N 21/00; G01N 21/85
[52] U.S. Cl. .......................... 162/263; 162/4; 162/49; 356/441; 356/442
[58] Field of Search .................. 162/49, 263, 198, 55, 162/4; 356/379, 380, 384, 441, 442; 364/502, 471

[56] References Cited

U.S. PATENT DOCUMENTS

| | | |
|---|---|---|
| 3,709,614 | 1/1973 | Hayakawa . |
| 4,184,204 | 1/1980 | Flohr . |
| 4,225,385 | 9/1980 | Hughes, Jr. et al. . |
| 4,276,119 | 6/1981 | Karnis et al. . |
| 4,318,180 | 3/1982 | Lundqvist et al. . |
| 4,342,618 | 8/1982 | Karnie et al. . |
| 4,374,703 | 2/1983 | LeBeau et al. . |
| 4,402,604 | 9/1983 | Nash . |
| 4,441,960 | 4/1984 | Karnis et al. . |
| 4,504,016 | 3/1985 | Wikdahl . |
| 4,514,257 | 4/1985 | Karlsson et al. . |

FOREIGN PATENT DOCUMENTS

| | | |
|---|---|---|
| 213285 | 9/1984 | Fed. Rep. of Germany . |
| 1068811 A | 6/1974 | U.S.S.R. . |

OTHER PUBLICATIONS

Carr; Seminar in China (paper presented) Oct. 1987.
"Detection and Quantification of Sticky Contaminants and Recycled Fiber Systems" by Doshi, Dyer and Krueger.
"Removing Stickies from Recycled Fiber" by W. C. Krueger and D. F. Bowers.
"Process Technology Solution for the Separation of the Sticky Impurities" by J. M. Voith GMBH of Heidenheim, Germany.
"Finns Ready 350-tpd TMP Mill, Reportedly First Under Computer Control" by Peter Inserra.

*Primary Examiner*—Steve Alvo
*Attorney, Agent, or Firm*—Andrus, Sceales, Starke & Sawall

[57] ABSTRACT

In a contaminant detector for processing paper pulp including sticky contaminants, a pulp sample is diluted to less than 0.5% consistency and passed through a concentrator from a plurality of classified samples having heavy and light particles. The inclined classified samples are again diluted to less than 0.5% consistency and passed as thin sample flow through an open channel having a light transmitting base. The flow is back lighted and a photodetector includes a linear array of sensitive elements aligned to receive the transmitted light. The sensitive elements aligned with particle creates a signal proportional to the width. By rapid sequential activation of the elements, a digital data stream is created which is processed by a microprocessor to determine the particle size and produce a plurality of contaminant relative signals related to different classified size ranges, such as heavy, medium and small contaminant particles. A particle removal includes sequential stages for successively removing the heavy, medium and small sized contaminants, with a control for each stage. The pulp sample is taken at a highest concentration location and the contaminant related signals are connected to actuate the corresponding controls for the several stages.

20 Claims, 3 Drawing Sheets

SYSTEM FOR MONITORING CONTAMINANTS WITH A DETECTOR IN A PAPER PULP STREAM

BACKGROUND OF THE PRESENT INVENTION

This invention relates to contaminant detection in paper pulp and particularly to the means to detect and measure the undesirable particles in virgin pulp and waste paper pulp including sticky contaminant particles in waste paper pulp for monitoring and controlling such particle inclusion in the pulp manufacturing process.

In the manufacture of paper products, an appropriate fiber pulp is used which may be purchased in solid pulp board form or directly processed in a liquid form. With recent development in the area of the environmental impact of processes, the increasing cost of energy and the like, the paper making industry has developed the recyling of waste paper into pulp for reconstitution into paper products.

It has long been known that the resulting paper product is of course greatly affected by the inclusion of foreign matter in the basic pulp from the which the paper product is made. Dirt, pitch, particles of bark, identified in the art as shives, and the like are the usual particles encountered in virgin pulp. Various means have been provided for detecting of the foreign contaminants during the forming of the pulp product and to modify the pulp forming process to minimize the inclusion of such foreign product.

Various systems have been suggested for monitoring the presence of such particles. Generally in the prior art, the pulp is sampled and the sample manually processed to detect the particle characteristic. The patent art discloses photodetection monitoring means for particles detection of pulp. For example, U.S. Pat. No. 4,402,604 which issued Sept. 6, 1983 and U.S. Pat. No. 4,225,385 which issued Sept. 30, 1980 disclose withdrawing of a sample of the pulp stock passing of the sample through a photoelectric detection system which detects the presents of dirt, shives and the like. U.S. Pat. No. 4,402,604 which issued Sept. 6, 1983 discloses a system whereby the liquid pulp or the pulp to be inspected is passed in a liquid state between a pair of transfer plates. The pulp is mixed with a pure liquid, that is, one without fiber content to control the consistency of the mixture as it passes through the plates. Light sources are applied to opposite sides of the moving sheet and a plurality of photosensitive devices are located in a row across the pipe to receive both reflected light and transmitted light. A series of photoelectric diodes are mounted across the plate to continuously scan the moving pulp. The output of each device is a signal dependent on the intensity of the light, and therefore the presence or absence of the particles. U.S. Pat. No. 4,225,385 discloses a method for directly passing of the pulp through a mixing unit for dilution of water and then through a inspection tube having a photoelectric device to scan the liquid as it passes through. Other patents have further considered analysis of the virgin pulp for foreign matter; for example, U.S. Pat. Nos. 4,184,204, 3,709,615, 4,318,180, 4,276,119, 4,441,960. The literature has also of course discussed the practical arts of foreign material detection.

Waste paper recycling further presents particularly unique problems in connection with foreign matter. Waste paper may originate from products including sticky contaminants. For example, the waste paper may include labels, tapes, and the like having an adhesive backing, as well as coated products including various adhesive material such as waxes, asphalt, polyethylene and other plastics. Such adhesive type materials create particularly unique problems not only with respect to the final product quality but serious difficulties in connection with the operating of the paper processing machinery. Thus, the "sticky" contaminants may agglomerate within the pulp or stock and result in a poor appearance of the final product, as well as adversely affect the end use properties required for certain application, such as printers and the like. In addition because of the adhesive characteristic, sticky contaminants are particularly prone to form deposits within the process machinery, impairing the runability and efficiency of the process machinery. Various methods have been suggested and used in connection with the processing of recycling of waste paper products. Generally, the techniques will include presorting of the paper to be recycled in an attempt to remove sticky material prior to pulping and processing. An alternative method is to treat the waste paper and/or the pulp so as to render the sticky contaminants innoxious, as by dispersion or treating for easy removal. This involves modifying the manufacture and/or formulation of the adhesives and other sticky contaminants to render them subject to such processing. Finally, a standard procedure used in paper pulping and making is to monitoring the contaminants and operate cleaning and removal devices in the pulping process.

The Institute of Paper Chemistry of Appleton, Wis. has been active in the development of appropriate detection systems. For example, a paper entitled "Detection and Quantification of Sticky Contaminants and Recycled Fiber Systems" by Doshi, Dyer and Krueger setsforth the difficulties encountered in recycling of paper because of sticky contaminants and as methods developed for detection and treating of such sticky contaminants. An article "Removing Stickies from Recycled Fiber" by W. C. Krueger and D. F. Bowers, both associated with the Institute of Paper Chemistry, appears in the July 1981 of "Tappi", Vol. 64 #7, Page 39–41. A further paper on the subject is published by J. M. Voith GMBH of Heidenheim, Germany, entitled "Process Technology Solution for the Separation of the Sticky Impurities" in the 1983 issue of "Pulping". All of the papers indicate the great difficulty which has been encountered in the removal of sticky contaminants and the difficulty of monitoring the presence of such materials.

Thus, the paper by Doshi et al is a somewhat typical approach presently used in the art. In such processes, the sample of the pulp either directly or after concentration of the contaminants in a sample is formed into a hand sheet and allowed to dry for handling. The air dryed hand sheet is placed between appropriate filter paper and hot pressed to form a sheet in which the contaminants can be monitored. The hand sheet is examined under ultraviolet light in accordance with the method developed by the authors. The authors found that the hot pressing method made invisible stickies visible and tended to increase or magnify the smaller sticky contaminants. The alternative generally is used in the art is a pure visual inspection of samples as to the size and number to the dirt particles. All such processes is obviously quite subjective, time consuming and provides for correction only after a long delay of the actual cycling of the apparatus.

There is therefore a very significant demand in the art for a method and means to detect and measure, and preferably control contaminant particles, particularly of sticky contaminants, in pulp preparation for the paper manufacture industry. The system should of course preferably provide an on-line measurement which produces a quantified output of dirt-type substances in the pulp preparation, and should permit both rapid analysis and creation of appropriate control signals to permit essentially on-line corrective action within the process.

SUMMARY OF THE PRESENT INVENTION

The present invention is particularly directed to a means and apparatus for monitoring the status of the contaminants, particularly including sticky contaminants in a liquid pulp, and in which an on-line signal may be generated for direct corrective action. Generally in accordance with the teaching of the present invention, a continuous sample of the fiber preparation pulp is withdrawn and specially process in a concentrating means for concentrating and separating contaminant particles into classification by specific gravity fractions, and then diluted to a significant degree. The separately classified and diluted contaminant sample or samples are passed through a monitoring device for monitoring the presence of the several classes of contaminants in the concentration pulp sample or samples. In a particularly unique and practical implementation, the pulp sample is passed through a sample concentrator and separator to separate basic pulp fibers from the pulp sample and to further divide the sample, into one or more separate classified samples of heavy and light contaminant particles. The separated classified sample is diluted and passed through a photodetecting unit which preferably includes a linear array of photosensitive elements. The classified sample is illuminated by special lighting arrangements such that the output of the linear array of photosensitive elements aligned with the sample develops a signal proportional to the width of the contaminant, and generates an appropriate signal such as a proportional analog signal. The signal is preferably processed to create a digital data stream which can be processed by a microprocessor to compare the characteristic with previously determined standards, and accurately determine the size of the contaminant and the character of the contaminant. Thus, the linear array may be activated in time spaced sequences to establish a series of digital signals which define the width and length of the several particles in the sample. By continuous monitoring of the data in relationship to such predetermined standards, both the quantity, size and distribution of the particles within the reduced fiber content pulp sample can be continuously analyzed. Corrective action based on such comparison and information can be introduced into the pulp preparation system through appropriate controls and feed back systems at different locations in the system for effective removal of contaminants. With the microprocessor processing of the data, the control can be affected essentially instantaneously in comparison to the more conventional manual control where correction may be delayed in terms of hours.

More particularly in a preferred construction of the present invention, the flow system is formed with a first cleaning stage havng means for successively removing large sized contaminants, medium sized contaminants and small sized contaminants. A second cleaning stage is connected to the last section of the first stage and has first and second section to remove successively smaller sized contaminants. A controller is provided for each stage. A concentration apparatus receives a continuous sample stream from the fiber preparation flow line at the inlet end of the cleaning line. The sample is passed through a dilution unit to substantially dilute the sample to less than 0.5%, with a range of 0.1% to 0.3% preferred. The concentrator separates the sample stream into a main fiber portion which is returned to the processing line and into a series of samples, related particularly to the different sized contaminant or specific gravity fraction samples, for example, into a heavy sample, a medium sample, and light sample for the first stage. The separated samples are then further diluted and passed through a photodetecting unit in the form of thin sheet-like flow of liquid. The photodetector flow passageway is an open channel unit to eliminate possible jamming of the passageway with foreign material. A linear array of photosensitive elements is transversly aligned with the sample flow. The array is illuminated through the stream from the side opposite the elements. The back lighting of the sample insures detection of all contaminants including the sticky contaminants. The illumination also establishes a reference potential related to the intensity of the light, with an analog signal output. Adjustable threshold points are inserted into the circuit to establish a digitized data stream. When a contaminant particle moves into the field of a photosensitive element, the contaminant particle blocks the transfer of light. Although various sticky contaminants are transparent, the backing lighting creates a shadow on the edges of the particle which will be detected by the photosensitive elements. The analog output level drops, and, depending upon the particular sensitivity of the system, decreases below the reference or threshold level. A substantial member of sensitive elements in the detection unit provides a means for detecting small or fine particulate contaminants. The digitized output is conveniently recorded and processed under microprocesser control essentially continuously, such as by establishing a new level every five milliseconds. The digitized data stream is stored in the microprocessor and rapidly processed through an appropriate program to determine the quantity and size distribution of the contaminants within the system. The microprocessor thus provides an effective means to correlate and analysis the relative state of the stock stream with respect to the several cleaning sections. The output is then connected into the process line to activate suitable controls at the different stages of screening and cleaning to maintain the stock pulp in a selective state. In the second stage, the controller determines large and relatively small or fine contaminants and generates corresponding outputs to the several cleaning sections to vary the effectiveness of the cleaning stations as necessary to establish the desired final product.

In this manner, the final product can be refined to the necessary degree to prevent contamination of the paper machinery as well as developing the necessary quality paper.

In a preferred application with the present invention, waste recycle pulp forming system includes a two stage monitoring for cleaning pulp of sticky contaminants and the like. The system particularly includes the usual preprocessing, followed by a first stage in which the pulp is sequential passed through a course cleaning section, a medium cleaning section and fine cleaning section. A second cleaning stage includes a fine cleaning section and final wash and bleach section. A first controller is coupled to monitor the pulp down stream of the course cleaning section and withdraws a diluted sample and fractionalizes the sample into three fractions including large or heavy contaminant sample, a medium contaminant sample and a third small or fine contaminant sample. The quantity of the contaminant of each sample is separately monitored by the controller and individual control signals are developed for each contaminant, and each control signal is coupled to control the corresponding stage. For example, the large size contaminant signal controls the input to the course cleaning section. The medium sized contaminant output signal is coupled to the medium cleaning section and so forth to monitor and control operation of the corresponding section. A separate controller similarly samples the pulp in the final section of the second stage. The second controller monitors a sample from a final bleaching section. The sample is thus again fractionalized into relatively fine and very fine contaminant particle samples and creates a pair of corresponding control signals to control a cleaning section and the final washing section immediately upstream of the bleaching section.

The final result is a clean pulp which can be used for production of high quality product and can be used without fouling the paper making machinery.

The controller is preferably constructed as an integrated unit including a sample separator and concentrator and a viewing apparatus. An input sample line is coupled to the process flow line through a dilution control box for establishing an appropriate sample for monitoring of the contaminants. The viewer includes an inclined flow channel. The concentrated samples are introduced into the flow channel, with further dilution thereof. The samples may be introduced as separate adjacent sheet-like flows or as a common flow of highly diluted contaminants samples. The linear array of sensitive elements scans the highly diluted contaminants sample and accurately determines any change in the relative level of the several contaminants. A suitable control unit is formed as part of the concentrator/viewer or as a separate unit and interconnected to the output of the concentrator/viewer for providing a feed back control through the processing line. A standard microprocessor has its input/output cable coupled to the concentrator/viewer through the control unit to close the control loop and provide for the desired control of the pulp cleaning system.

The concentrator may be of any suitable construction such as well known centrifugal concentrator which separates the main sample into the several fractionalized samples for different sizes of the contaminants.

The present invention thus provides an on-line control apparatus and method for improving fiber preparation for the pulp manufacturing industry by detecting, measuring and controlling contaminant particles and in particularly sticky contaminants in the raw materials and in particularly waste product raw materials. The apparatus with the on-line feature essentially eliminates the long delay heretofore encountered in the modification of the pulp, and through its rapid measurement of size and quality of contaminants establishes and maintains a uniform product necessary for high quality pulp. The apparatus basically uses commercially available components which can be appropriately constructed and arranged to conjointly operate to establish and produce the desired continuous on-line control.

BRIEF DESCRIPTION OF DRAWINGS

The drawings furnished herewith illustrate the best mode of carrying out the present invention.

In the drawings.

DESCRIPTION OF THE ILLUSTRATED EMBODIMENT

Figure 1:
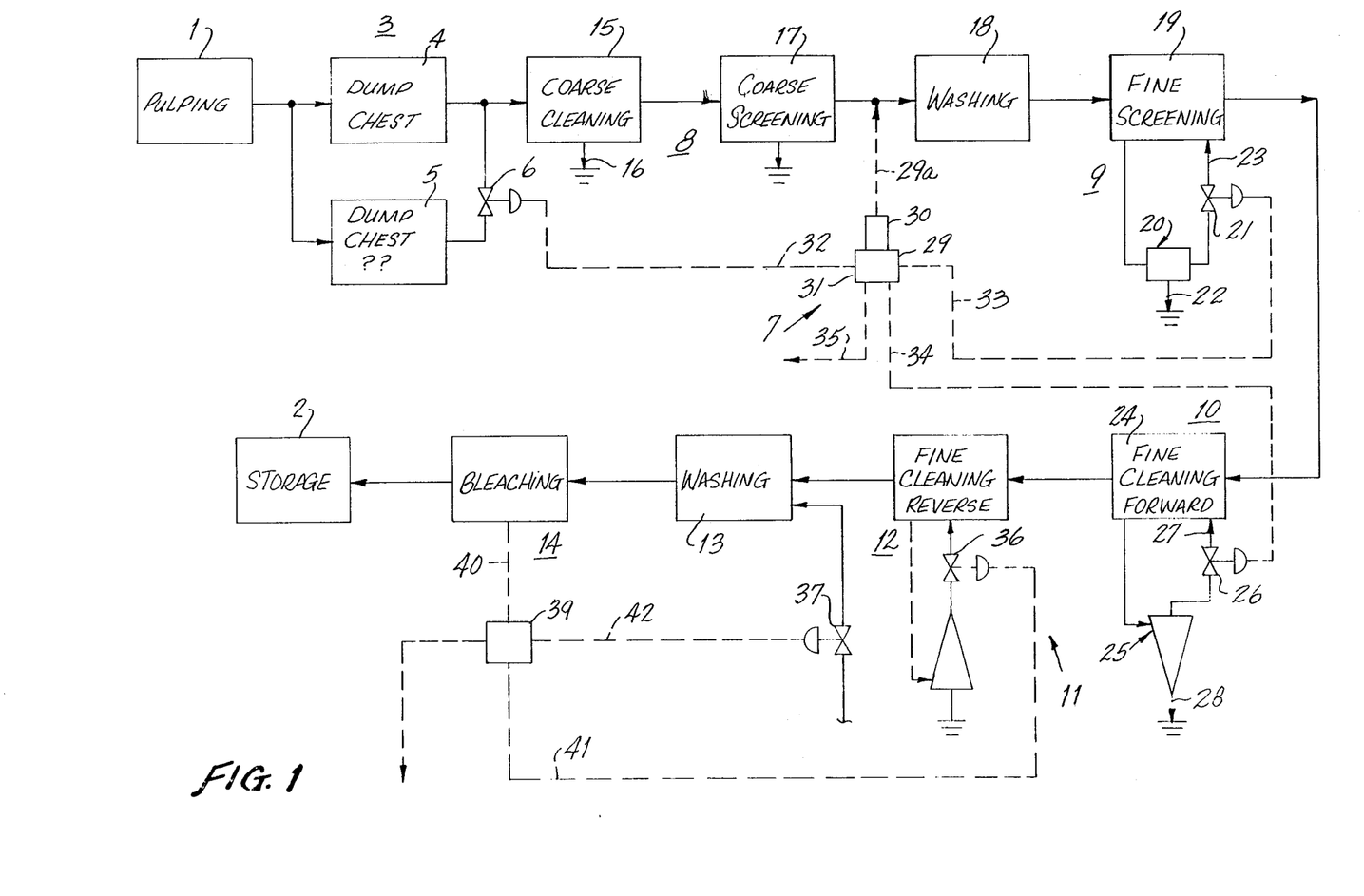
FIG. 1 is a block diagram of a pulp cleaning system including a two-stage monitoring system in accordance with the teaching of the present invention to produce a uniform high quality pulp product.

Referring particularly to FIG. 1, a pulp cleaning line or system is illustrated having its input connected to the pulping apparatus 1. The pulp is passed through the system and cleaned pulp is applied to a storage unit 2 in the illustrated embodiment of the invention. In actual practice of course, the clean pulp may be connected directly into an appropriate paper forming line or the like. The pulp is passed through a multiple stage particle removal system including an input section 3 for receiving of the stock stream of pulp from the pulping apparatus 1. The input section 3 includes a main container 4 identified as a dump chest. An excess contaminanted pulp container 5 is connected in parallel with the dump chest 4 and includes a control valve 6 for varying the transfer of pulp from the container 5 into the downstream cleaning system.

The particle removal system is shown as a two-stage system including a first stage 7 having a coarse contaminant removal section 8, a medium contaminant removal section 9 and a fine contamiant removal section 10. A second stage 11 connects section 10 to the storage unit 2. The second stage 11 includes a fine contaminant cleaning section 12, a final wash section 13 and a bleaching section 14.

The coarse removal section 8 includes a coarse cleaner 15 for removing of a portion of the stock stream with a concentration of large sized contaminants, as at 16. A coarse screen unit 17 is connected downstream from the coarse cleaner 16. The output of the course screen unit 17 is a pulp with a selected minimal level of the large sized contaminants.

The coarse cleaned stock stream is sent to the second removal section 9, consisting of the wash unit 18, discharging into a final medium contaminant screen unit 19. The screen unit 19 is constructed and arranged to remove relatively medium sized contaminants. The fine screen unit 19 may be a multiple stage unit with a final fine screen "accept" control 20. A control valve 21 controls the relative flow to a reject line 22 and an "accept" line 23, which supplies the medium cleaned stock to section 10. The final contaminant cleaning section 10 is shown including a fine cleaning "forward" unit 24 with its input connected to the output of section 9. The "forward" unit 24 is a multi stage unit and includes an "accept" control unit 25 having a control valve 26 for controlling the output flow of the stock stream between an "accept" line 27 to the second stage 13 and a reject line 28. The control valves 6, 21 and 26 of the first particle removal stage 7 are all interconnected to an automatic on-line monitor controller 29 to produce an automated control of the several valves in response to the level of the several classified contaminants in the main supply, as follows.

The controller 29 has an input line 29a connected to the main line from the coarse screen unit 17 to create a sample stream of the pulp, by withdrawing a continuous stream of the coarse screened pulp, diluting such sample, passing such sample through a special concentrator 30 for fractionalizing of the sample into a plurality of samples such as a large contaminant sample, a medium contaminant sample and a small or fine contaminant sample. The creating of the three samples is disclosed for purposes of explanation of the illustrated multiple stage particle removal system. As more fully discussed hereinafter, the concentrator 30 may be constructed to produce more or less than three sample streams and may even create a single stream to be monitored, with classification of contaminants created within a monitoring unit. Further, the stock stream may be sampled at other than the illustrated location. However, the connection to the stock stream at the coarse screen unit 17 is at a point of maximum reject concentration and produces a high level of reject sensitivity for monitoring and controlling the several stages.

The concentrated samples are further diluted and passed through a photodetector unit 31 for individually monitoring the relative quantity of the corresponding contaminant in the course cleaned pulp and in developing control signals in accordance with the measured condition at three corresponding outputs 32,33 and 34. A reference for each level is set in the unit 31, as at 35. The large contaminant signal is coupled to the dump chest control valve 6. The medium sized contaminant signal output 33 is coupled to the screen accept control valve 21 and the small or fine contaminant related signal output 34 is coupled to the last stage of the fine cleaned forward accept control valve 26.

The output of the fine clean forward section 10 is coupled to the second cleaning stage 11 consisting of the fine clean reverse unit 12, the washing unit 13 and the bleaching unit 14. The unit 12 including an "accept" control valve 36 and the washing unit 13 includes a dilution control valve 37 for controlling the proportion of the contaminants per unit of stock flowing therefrom. A second controller 39 which may be identically constructed to the controller 29, continously draws a sample of pulp from the bleaching unit 14 via input sample line 40. The second controller 39 again dilutes the sample, separates the bleached pulp into a small contaminant size sample and very small contaminant sized sample, further dilutes the samples and creates corresponding output signals. The small contaminant sized output line 41 is coupled to "accept" control valve 36 and adjust the functioning of the fine cleaner 12 to control the contaminant content with respect to the desired reference. Similarly, the very small contaminant signal line 42 is coupled through the washer dilution control valve 37 for varying the dilution in the washing unit 13 and thereby the relative level of the very fine contaminants in the stock stream fed to and through the bleaching unit 14.

The output of the second stage 11 is a highly refined and clean pulp.

Each of the processing units diagrammatically illustrated in FIG. 1 are known devices presently used in pulp processing and formation. The present invention is particularly directed to the method and apparatus providing a continuously monitored stream, with an output related to the contaminants and in a preferred system, having the output connection into a closed loop control to maintain the continuous modification of the cleaning and separating process to establish optimun on-line system operation.

Figure 2:
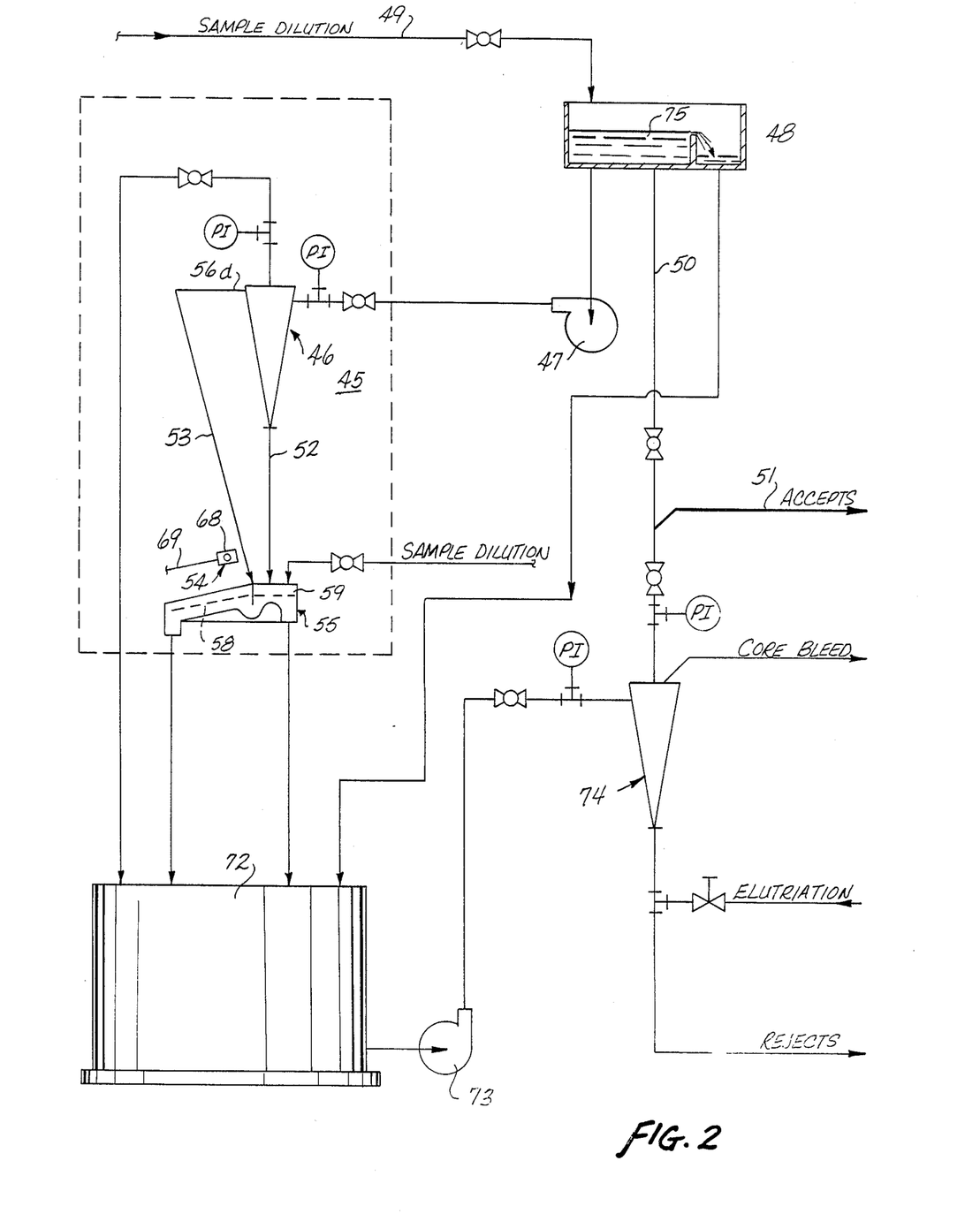
FIG. 2 is a simplified illustration of a controller shown in FIG.1.

Although various methods and monitoring means may be developed by those skilled in the art based on the teaching herein, a simplified block diagram illustation of a preferred construction is shown in FIG. 2, for each of the monitors units shown in FIG. 1.

Referring particularly to FIG. 2, a sample concentrator and viewer 45 is diagrammatically shown including a suitable separator and concentrator 46 for developing a furst sample stream and a second sample stream. A sample pump 47 is shown having its input connected to a sample dilution box 48. The sample dilution box 48 is connected to clear water source or line 49 and a sample line 50 from the process line 51, and generates a sample having a consistency of a range generally between 0.1 and 0.3%. The output of the sample pump 47 is applied to the cyclone separator 46 which separates the sample into a plurality of different sample streams. Thus, the centrifical action on the sample results in the separation of the sample into various readily dispersed levels which can be withdrawn from various portions of the separator 46 and including an accept stream having the desired fibers concentrated therein. This latter fiber laden stream is returned as at 51a to the processing line. The heavier contaminants are concentrated in the outer portion of the separator 46, with the lighter contaminants carried through the accept end of the unit 46. In the structures of FIGS. 2-6, a pair of concentrated streams 52 and 53 are transmitted in the concentrated form to a viewer 55 having a photodetection device 54 mounted to monitor the contaminant level in the streams 52 and 53. The contaminant concentrated samples are further diluted at the viewer to reduce the consistency within the viewer 55. For example, the concentrated samples may be reduced to have a consistency of approximately 0.2% to 0.4%. The streams are fed through the viewer 55 at an appropriate rate, for example, such as 1 to 4 ft. per second, and the contaminant level monitored and classified within the operation of the viewer.

Figure 3:
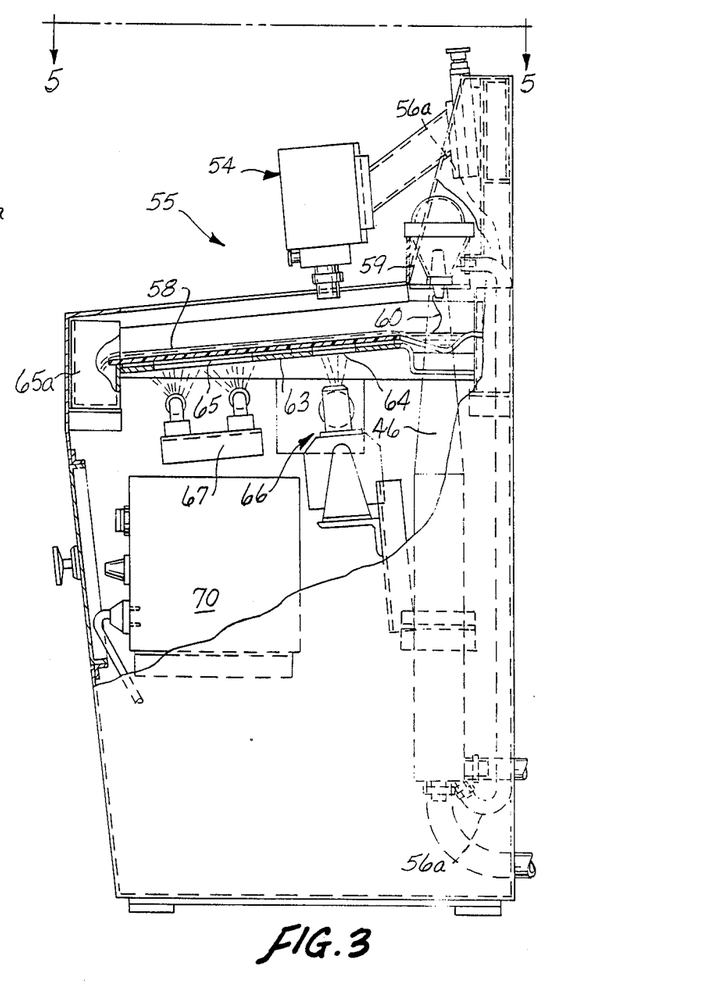
FIG. 3 is a pictorial illustration of the control system shown in FIGS. 1 and 2.
Figure 4:
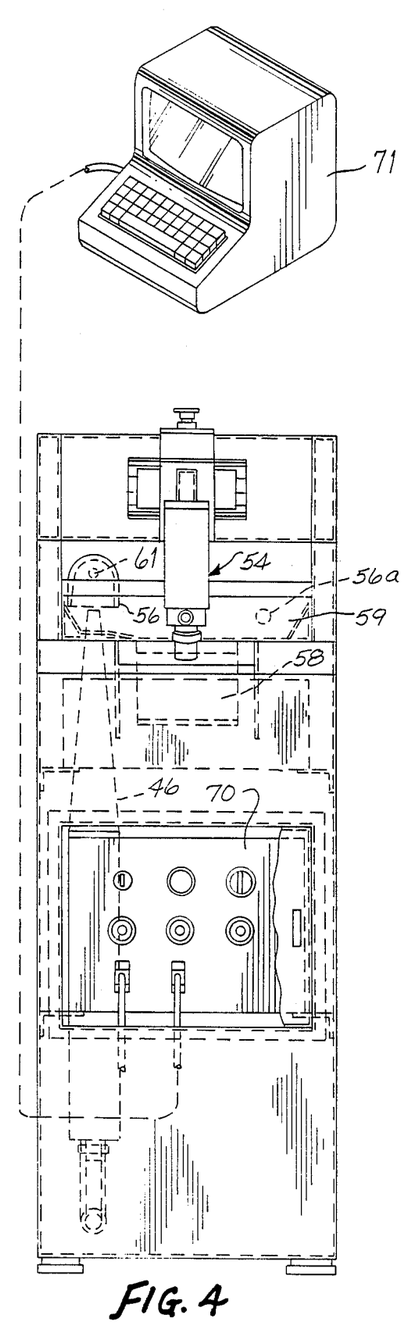
FIG. 4 is a front view of controller with parts broken away to show detail construction.
Figure 5:
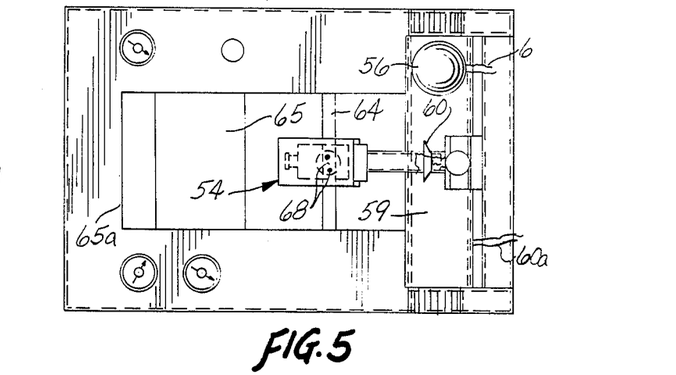
FIG. 5 is a view taken generally on line 5—5 of FIG. 4.

The separator and concentrator 46 may be a multiple stage cyclone unit including a first stage to separate the coarse contaminant from the medium and fine contaminants and a second stage to separate the medium and fine contaminants. Alternatively, a single stage unit may be provided to separate out the contaminant into a pair of concentrated streams, as shown in FIGS. 2-5. For example, a reverse flow type cyclone unit 46 is shown in FIGS. 3-5 as a single stage unit. In the reverse flow unit, the heavy and medium contaminants are concentrated in the outer portion of the unit 46 and discharged through the top underflow tip into a discharge cup 56 and therefrom into a passageway in the viewer as hereinafter described. The accept flow with the small contaminants therein reverse from the upward flow path and move downwardly through the center of unit 46 and pass from the bottom overflow back to the supply tank. A core bleed line 56a at the bottom overflow is used to sample the accept flow and generate a fine contaminant sample flow which is essentially free of the usual fiber in the original sample and the accept flow which is returned to the processing line. The line 56a is coupled to the flow passageway in the viewer 54 to combine the sample from line 56a with the flow from the discharge cup 56. The efficiency of cyclone concentrater is controlled in the usual procedure by control of the several known parameters such as in conventional centrifugal cleaners.

Although the classification may vary in any given pulp processing line, a typical classification for processing a random assortment of waste paper pulp with the contaminants classified by size would include large or heavy contaminants as 1.2 mm (millimeters) or larger, medium contaminants as 0.6 to 1.2 mm and small or fine contaminants as 0.1 to 0.6 mm. The density or specific gravity of the contaminants may vary within such ranges and between ranges, but the concentrator will separte out the several contaminants upon a consistent and repeatable basis.

Further, in processing of waste paper, the pulp samples are water based and few of the pulp fibers are present in the samples. Thus, the highly diluted sample and the efficiency of concentrator and separator devices effectively separates the sample into a plurality of flows including one or more streams within which the contaminants have been concentrated and a remaining accept stream which includes essentially all of the desirable fiber content of the original sample and from which the contaminants have been substantially removed. For example, various centrifugal separators are commercialy available from the Bird Machine Company, Inc. of So. Walpole, Mass. and the Black Clawson Company of Midletown, Ohio.

The dilution of the sample from the dilution box to a consistency of 0.1 to 0.3 per cent is a consistency level substantially below the accepted level in more conventional practice. The centrifugal concentrators are highly effective and the resulting classified sample establish an effective sample even though highly diluted. Further, in the medium to fine or small concentrator, the highly dilute sample is desirable to more fully remove the desirable pulp fibers with the accept flow from the concentrator. Thus, the classified sample passed to the viewer 55 more accurately reflects the actual contaminant level in the original sample.

The viewer 55 is specially constructed to establish a generally flat or thin stream through one or more adjacent passageways in the viewer 55 for the contaminant concentrated stream from cup 56 and bleed line 56a. A photodetection unit 54 is specially constructed to scan the sample streams in the viewer 55.

The illustrated viewer unit 55, as more fully shown in FIGS. 3 and 5, includes an essentially open flow channel 58 connected to receive the classified samples 52 and 53. The inlet to the channel 58 includes a mixing box 59 connected to the cup 56 and to the bleed tube 56a. The mixing box or tube 59 combines the two separate flows at a discharge outlet, at which a classified sample flow sinuous dispersal plate 60 directs the flow into the channel as a distribued stream. The mixing box 59 if also coupled to a sample dilution line 61 for additional dilution of the samples to reduce the consistency of the concentrated classified sample. In the illustrated embodiment, the dilution line 61 is coupled to the discharge cup 56. Although not critical, the sample flow as discharged is diluted to a consistency of about 0.2 to 0.4 percent.

The channel 58 is formed as a relatively wide and thin flow passageway. The bottom wall 62 is clear plastic and is inclined to establish a gravity flow such that the sample flow is in the form of a thin sheet, with the corresponding contaminants dispersed throughout the flow. The channel may have a width for example of four inches, with a flow rate producing a flow ⅛ inch in depth maximum. The flow rate may conveniently be set to approximately 1 to 4 feet per second.

A see-through cover, not shown, maybe placed over the channels, but is not considered necessary in a practical application to permit viewing of the samples for visual inspection. The coyer, if used, is however spaced above the designed maximum flow level such that the essentially free flow stream of diluted sample is not disturbed. The sample flow discharges into a return channel 65a connected to discharge the sample to a waste system or for recycling.

The dilution of the classified sample and the free flow stream are significant to establish an effective continuous monitoring of the pulp contaminant content, particularly where significant "sticky" contaminants are present. The contaminants will tend to adhere to the walls of the flow passageway and interfere with the flow as well as distort the apparent level of contaminants in the flow. Although the photodetector open channel flow passageways may need periodic cleaning to maintain the desired degree of accuracy, the open structure and high dilution as well as the appropriate rate of flow in the inclined channel significantly minimizes such problems satisfactory on-line type monitor.

In a practical structure such as shown in FIGS. 4 and 5, the bottom wall 62 is supported on a metal back wall 63 having a first narrow photo detection slot 64 adjacent the upper end and a wide visual viewing opening 65 spaced outwardly therefrom.

A back lighting unit 66 such as a power line driven incondescent lamp is located beneath the bottom wall in alignment with the photodetection slot 64. The back lighting unit 66 illuminates the sample flow and transmits the light upwardly therefrom. The level of the transmitted light is directly controlled by the level of contaminants in the classified sample passing through the detection channel and part slot 64. Various contaminants such as various clear plastic particles and other "sticky" contaminants may transmit light. However, even such contaminants with back lighting create edge shadows and thereby varies the illumination level when viewed from the top or upper side of the channel. Thus, the illustrated embodiment particularly avoids both front and back lighting which would tend to destroy the "shadow" effect and prevent accurate detection of certain contaminants. However, special limited front illumination such as with an ultraviolet source may enhance the shadow effect and of course be used.

A dual florescent lamp unit 67 is shown located beneath the visual display opening 65. The lamp unit 67 illuminates the flow and highlights the contaminants for visual inspection. An experienced person can monitor the flow condition.

The photosensitive unit 54 is movably mounted to the top frame of the sample viewer 55. For example, the unit 54 may be a commercial line scan camera such as a model CCD camera commercially available from Fairchild Camera and Instrument Corporation. The camera 54 includes a linear array photo sensistive imaging elements 68 which in the CCD model camera are charge-coupled devices. The output of the charge-coupled devices are suitably processed to produce an analog video output signal which has an instantaneous amplitude representing the spatial distribution of image brightness along the row of the imaging element. The output of adjacent devices is therefore a signal directly representing the width of the contaminant in the classified sample being viewed by the camera.

A single camera 54 is shown movable mounted over a viewing position of the channel. The camera 54 may thus be moved to scan different areas of the channel, or if separate flows are established, to monitor each stream. The camera 54 may be moved either manually or through an automated positioning control.

In a continuous monitoring and flow control system where individual sample streams are provided, a plurality of individual cameras may be used to separately monitor each classified sample at a desired periodic rate for developing an appropriate control signal for controlling of the valves 6, 2 and 26 or other cleaning control devices.

The photosensitive array thus scans a given width in the aligned channel. The scan width will generally be less than the total width of the channel. However, the contaminant will be essentially uniformily dispersed over any reasonable volume of flow and sensing of a portion of the total flow in a closely spaced sequence will produce an accurate measurement of the contaminant content. For example, in a practical construction, the width of a channel may be four inches and the camera scan length may be one inch.

The camera includes the various necessary associated parts such as the necessary lens, signal processing and control circuits. The control unit for the camera will of course includes various functional controls including the video output control, video data rate control, exposure control and camera power supply control. As these and similar specifics of the photodecting device are commercially available and readily understood by those skilled in the art no further description of the camera is given herein, other than as such may be used in operating the photodector unit in the illustrated embodiment of the invention.

In particular, the row of photosensitive elements 68 are mounted as a linear row or array. The array is located transverse of the path of the flow streams and continuously monitor the flow through the passageway.

Each element 68 produces a signal level proportional to the incident light. In the absence of a particle, maximum illumination is created. Movement of a particle in alignment with the element reduces the illumination, essentially in proportion to the size of the element and the output of the element correspondingly is reduced. The output of each is therefore a proportionate analog signal transmitted via an output line 69.

The classified outputs are connected to a logic controller 70 which may be a suitable hard wired servo type control unit, or advantageously may include a microprocessor 71 which processes the signals and establishes proper signals at lines 32,33 and 34 of FIG. 1.

The monitor system as shown does not attempt to necessarily measure the actual count of the particles but rather the ratio or precentage changes of the contaminant in the continuous sample. The system must however establish a high degree of repeatability such that similar classified samples passed through the viewer give the same output. Thus in a control system, the control signal must accurately reflect whether or not the contaminant level has increased or decreased so that the system control can be appropriately changed.

The discharge from each of the viewer sections and from the dilution tank or box returns to the main system, shown as a supply tank 72. A supply pump 73 continuously withdraws the pulp from the tank. The pulp stream is sent to a particle removal station or section, which may be a simple screen device such as shown in FIG. 1 or a cyclone type separator 7 such as shown in FIG. 2. The particle removal device is not critical and will be determined by the location at which the sample is to be taken.

The sample dilution box 48 is shown coupled via line 50 to the accept line of the cleaning unit to continuously transmit a sample of stock stream of pulp back to the dilution box 48 for dilution with the incoming dilution water.

The pulp sample is taken at a point in the system which preferably has a maximum reject concentration. In the system of FIG. 1, for example, the sample is taken at the input of each cleaning section. This maximum reject sample point creates a highest level of reject sensivity for contaminant detection.

The sample dilution box 48 may be of any suitable construction and is diagrammatically shown including an overflow chamber 75 into which the sample is continuously supplied in combination with a portion of a pure water from line 49. The sample pump 47 continuously withdraws the diluted sample, and processes the sample through the concentrater 46 and the viewer 55 for detecting the contaminant and producing a reusable output, as described above.

The present invention provides an apparatus and method for continuously monitoring in real-time the state of a paper making pulp and permits on-line controlling of the pulp conditions. The system provides accurate and highly repeatable contaminant level determination for improving the control of the processed pulp.

Various modes of carrying out the invention are contemplated as being within the scope of the following claims particularly pointing and distinctly claiming the subject matter which is regarded as the invention.

I claim:

1. A system for monitoring a stock stream of paper pulp in a flow line for continuously monitoring contaminanats in said stream, comprising means coupled to the flow line for continuously withdrawing a sample stream of the stock stream at a point of significant reject concentrations, concentrating means for treating said sample to separate said pulp sample into a plurality of classified sample streams wherein at least one of said classified sample streams includes a concentration of the contaminant particles, and monitoring means to monitor said stream and determine the realtive level of the different contaminants in said monitored classified sample stream, said monitoring means including a dispersal flow means having a relatively wide and thin passageway means receiving said classified sample stream means to supply said classified sample stream to said passageway means at a flow rate establishing an essentially free flowing stream having a maximum level in said passageway means and an open space above said maximum level of said free flowing stream, and photodetector sensing means coupled to said free flowing stream to detect the contaminants therein.

2. The system of claim 1 including means to dilute said pulp sample stream from said stock stream, means to dilute the classified sample stream being monitored from said concentrating means, and said monitoring means including said photodetector sensing means coupled to said classified sample stream and operable to detect the size of a contaminant particle and classify the contaminants into selected different size classifications.

3. The system of claim 1 including means to dilute said pulp sample stream to a consistency less than 0.5%.

4. The system of claim 1 including a particle removal system for reducing the level of said contaminants in said stock stream, and means in spaced portions of said removal system to modify the concentration of the said contaminants in said stock stream in accordance with variation with the output of said monitoring means.

5. The systems of claim 4 wherein said monitoring means includes a first monitor connected to monitor the stock stream downstream of a supply and including means for adding a relatively high contaminant supply to said stock stream, said monitoring means establishing a heavier contaminant signal connected to actuate said means for adding the contaminant supply to said stock stream in response to a selected decrease in the contaminant related signal of said monitor.

6. The system of claim 1 includes a cleaning section with means for separating of the stream into a reduced contaminant concentrating accept flow and an increase concentrating reject flow, said controller having a contaminant output means connected to vary the accept flow relative to said reject flow and thereby vary the contaminant level in the accept flow to maintain a predetermined consistency levels.

7. The system of claim 1 wherein said monitoring means including said dispersing flow means coupled to said concentrating means, said flow channel developing said free-flow stream as a relatively thin and wide flow of said classified sample being monitored, lighting means for back lighting of said flow channel for illuminating said classified stream and developing a shadow effect on transparent contaminants, and said photodetector sensing means mounted to the front side of the channel to detect the several contaminants in said classified sample.

8. The system of claim 7 wherein said photodetector sensing means is a high speed camera device including a linear array of photosensistive elements operable to monitor the width of the contaminant, and means to actuate said camera at a rate sufficient to monitor the length of said contaminants and thereby determine the relative size of the contaminant.

9. The system of claim 1 wherein said passageway means includes a flow channel coupled to said concentrating means to receive said classified sample, said channel having a wide base to establish said free flow streams as a thin and wide sheet-like flow of a substantially uniform depth, and said sensing means being located in alignment with said channel to detect and classify the several contaminants in said sheet-like flow.

10. The system of claim 9 wherein said concentrating means establishes a first sample stream including the larger contaminants and a second sample stream including the smaller contaminants, and means to introduce said sample streams to said flow channel in side-by-side relationship.

11. The system of claim 9 wherein said sensing means includes a linear array of photosensitive elements mounted transerse of said channel and periodically operated at a rate to sequentially determine the width of the contaminant aligned therewith.

12. A waste paper pulp porcessing apparatus for monitoring the changes in contaminant levels in pulp stream, comprising a sample means for withdrawing a pulp sample from said pulp stream, a separating means connected to said sample means for separating from said sample a contaminant portion of the sample essentially free of paper forming fibers and having a substantial portion of selected contaminants of said pulp sample, a dispersal flow means having a relatively wide and thin flow passageway, means to supply said classified sample stream to said passageway at a flow rate establishing an essentially free sheet-like flowing stream of said contaminant portion of the sample in said passageway, having a maximum level in said passageway and an open space above said maximum level of said free flowing stream, a photodetector means adjacent said passageway having a linear array of photosensitive element located across said passageway and establishing adjacent sensing areas on the order of micrometers, and back lighting means located to the opposite side of the passageway from said linear array of phtosensitive elements.

13. The waste paper pulp processing apparatus of claim 12 including an ultraviolet radiation source mounted to the front side of said channel to enhance said shadow effect.

14. The waste paper pulp processing apparatus of claim 12 including a liquid dilution source coupled to said viewer for adding a pure contaminant portion prior to passage of said portion past said linear array of photosensitive elements.

15. The apparatus of claim 12 wherein said photodectector means is a high speed camera wherein said array has an operative length less than the width of said channel.

16. The apparatus of claim 15 including a movable support for said photodetector means for positioning of said camera in alignment with different portions of said channel.

17. The apparatus of claim 12 wherein said separating means establishes a plurality of separate concentrate samples, and said channel means esablishes essentially separate flow of said contaminant samples.

18. The apparatus of claim 12 wherein said channel means includes a rectangular U-shaped channel member having a light transmitting bottom wall, said bottom wall being inclined to establish a gravity flow of said sample, the depth of said channel being greater than the maximum depth of said sample flow.

19. The apparatus of claim 18 including a transparent cover secured to the top of said channel for visual viewing of said flow in said channel member.

20. The system of claim 12 wherein said photodetctor device includes a linear array of photosensitive elements to define a continuous columnar light sensor, each of said elements sensing a length on the order of 10 micromenters, means to process the output of said photosensitive elements relative to each other to detect the width and length of said contaminant particles.

* * * * *